US010324100B2

(12) United States Patent
Fujino et al.

(10) Patent No.: US 10,324,100 B2
(45) Date of Patent: Jun. 18, 2019

(54) METHOD FOR QUANTIFYING PLASMALOGENS USING PLA1 PROCESSING

(71) Applicant: Institute of Rheological Functions of Food, Fukuoka (JP)

(72) Inventors: Takehiko Fujino, Fukuoka (JP); Shiro Mawatari, Fukuoka (JP)

(73) Assignee: Institute of Rheological Functions of Food (JP)

( * ) Notice: Subject to any disclaimer, the term of this patent is extended or adjusted under 35 U.S.C. 154(b) by 29 days.

(21) Appl. No.: 15/478,487

(22) Filed: Apr. 4, 2017

(65) Prior Publication Data

US 2018/0284143 A1    Oct. 4, 2018

(51) Int. Cl.
| | |
|---|---|
| *G01N 33/92* | (2006.01) |
| *C07F 9/10* | (2006.01) |
| *C12Q 1/28* | (2006.01) |
| *C12Q 1/26* | (2006.01) |
| *C12Q 1/44* | (2006.01) |
| *G01N 33/52* | (2006.01) |

(52) U.S. Cl.
CPC .......... *G01N 33/92* (2013.01); *C07F 9/103* (2013.01); *C12Q 1/26* (2013.01); *C12Q 1/28* (2013.01); *C12Q 1/44* (2013.01); *G01N 33/52* (2013.01); *G01N 2333/92* (2013.01); *G01N 2800/04* (2013.01); *G01N 2800/042* (2013.01); *G01N 2800/28* (2013.01); *G01N 2800/2814* (2013.01); *G01N 2800/2835* (2013.01); *G01N 2800/2864* (2013.01); *G01N 2800/323* (2013.01); *G01N 2800/50* (2013.01)

(58) Field of Classification Search
CPC .... G01N 33/92; G01N 2333/92; C07F 9/103; C12Q 1/28; C12Q 1/26
See application file for complete search history.

(56) References Cited

FOREIGN PATENT DOCUMENTS

| JP | 2016045112 A | 4/2016 |
|---|---|---|
| JP | 2016111929 A | 6/2016 |
| WO | 2012090625 A1 | 7/2012 |
| WO | 2016092878 A1 | 6/2016 |
| WO | 2016181491 A1 | 11/2016 |

OTHER PUBLICATIONS

Murphy et al. Acidic Hydrolysis of Plasmalogens Followed by High-Performance Liquid Chromatography; Lipids, vol. 28, No. 6, pp. 565-568. (Year: 1993).*

Mawatari et al. Simultaneous Preparation of Purified Plasmalogens and Sphingomyelin in Human Erythrocytes With Phospholipase A1 From Aspergillus Orizae; Bioscience Biotechnology and Biochemistry, vol. 73, No. 12, pp. 2621-2625. (Year: 2009).*

Mawatari, et al., "Measurement of Ether Phospholipids in Human Plasma with HPLC-ELSD and LC/ESI-MS After Hydrolysis of Plasma with Phospholipase A1", Lipids vol. 51, pp. 997-1006, Jul. 7, 2016.

Goodenowe, et al., "Peripheral ethanolamine plasmalogen deficiency: A logical causative factor in Alzheimer's disease and dementia", Journal of Lipid Research, vol. 48, pp. 2485-2498, Aug. 2, 2007.

Mawatari et al., "Separation of intact plasmalogens and all other phospholipids by a single run of high-performance liquid chromatography" Analytical Biochemistry, 370, p. 54-59, May 26, 2007.

Ifuku et al., "Anti-inflammatory /anti-amyloidogenic effects of plasmalogens in lipopolysaccharide-induced neuroinfflammation in adult mice", Journal of Neuroinflammation 9:197, p. 1-13, Aug. 13, 2012.

Katafuchi et al., Effects of Plasmalogens on Systemic Lipopolysaccharide-induced Glial Activation and ?-amyloid Accumulation in Adult Mice, Annals of the New York Academy of Science, vol. 1262, Issue 1, p. 85-92, Jul. 2012.

Yamashita et al., "Preparation of Marine Plasmalogen and Selective Identification of Molecular Species by LC-MS/MS", Journal of Oleo Science, Volune 63, Issue 5, p. 423-430, Apr. 9, 2014.

Hossain et al., "Plasmalogens Rescue Neuronal Cell Death through an Activation of AKT and ERK Survival Signaling", PLOS One, vol. 8, Issue 12, p. 1-14, Dec. 20, 2013.

Fujino et al., "Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial", EBioMedicine vol. 17, p. 199-205, Feb. 24, 2017.

Oma et al., "Changes in Phospholipid Composition of Erythrocyte Membrane in Alzheimer's Disease", Dement Geriatr Cogn Disord Extra vol. 2, p. 298-303, Aug. 15, 2012.

* cited by examiner

*Primary Examiner* — Sharmila G Landau
*Assistant Examiner* — Paul C Martin
(74) *Attorney, Agent, or Firm* — Lerner, David, Littenberg, Krumholz & Mentlik, LLP

(57) ABSTRACT

The present invention provides methods for quantifying an amount of plasmalogens in samples with high accuracy in an easy, convenient and inexpensive manner by using a hydrolysis processing to samples and a lipid extraction followed by the measurement using High Performance Liquid Chromatography (HPLC) with Evaporative Light Scattering Detector (ELSD) or Mass Spectrometer (MS), a fluorescence plate reader or a plate reader. The present invention also relates to a method for examining a subject by using the above method, a biomarker for disease detection, a method for using the biomarker for the disease detection, as well as a kit for the disease detection.

8 Claims, 9 Drawing Sheets

(a)

(b)

(a)

(b)

METHOD FOR QUANTIFYING PLASMALOGENS USING PLA1 PROCESSING

FIELD OF THE INVENTION

The present invention relates to a method for quantifying plasmalogens, in other words, a method for measuring the amount of plasmalogens in samples, in particular serum or plasma samples.

More specifically, it relates to a method for measuring the amount of plasmalogens in samples with high accuracy in an easy, convenient and inexpensive manner, using High Performance Liquid Chromatography (HPLC) with Evaporative Light Scattering Detector (ELSD) or Mass Spectrometer (MS), a fluorescence plate reader or a plate reader. The present invention also relates to a method for examining a subject by using the above method, a biomarker for disease detection, a method for using the biomarker for the disease detection, as well as a kit for the disease detection.

BACKGROUND OF THE INVENTION

Glycerophospholipids present in a living body of mammals, such as humans, comprise:

(1) phospholipids having an ester bond at the sn-1 position of the glycerol backbone (diacyl phospholipids); and (2) phospholipids having an ether bond at the sn-1 position (ether phospholipids).

The ether phospholipids comprise:

(1) phospholipids having an ether bond at the sn-1 position (alkyl acyl phospholipids); and (2) phospholipids having a vinyl ether bond (alkenyl acyl phospholipids).

Those having a vinyl ether bond (alkenyl acyl phospholipids) are also referred to as plasmalogens. A general formula of plasmalogens is described below:

[Chemical Formula 1]

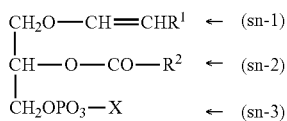

In the above formula, $R^1$ and $R^2$ represent an aliphatic hydrocarbon group.

$R^1$ at the sn-1 position is usually an aliphatic hydrocarbon group having 1 to 20 carbon numbers, such as dodecyl group, tetradecyl group, hexadecyl group, octadecyl group, icosanyl group, etc.

$R^2$—CO at the sn-2 position is usually an polyunsaturated alkyl carbonyl group derived from polyunsaturated fatty acids, such as octadecadienoyl group, octadecatrienoyl group, icosatetraenoyl group, icosapentaenoyl group, docosatetraenoyl group, docosapentaenoyl group, docosahexaenoyl group, etc.

X at the sn-3 position represents a polar group in the above formula. Preferably, X is ethanolamine, choline, serine, inositol or glycerol.

In ether phospholipids of a mammal such as a human, alkyl acyl phospholipids are present in a very few amounts, while most are alkenyl acyl phospholipids, i.e., plasmalogens. Moreover, in such a mammal, there are a few plasmalogens having serine or inositol, while most of them have ethanolamine or choline. Furthermore, in a living body, the ether phospholipids are mainly contained in a biological membrane (cell membrane), so are other phospholipids.

The amount of ether phospholipids, such as plasmalogens, for example, as shown in Patent Document 1, is often measured by using red blood cell samples.

Recently, it was reported to suggest that the amount of plasmalogens in serum is low in patients with severe disease such as dementia, and Alzheimer's disease (for example, see Non-Patent Document 1). Furthermore, it is suggested that the amount of plasmalogens in serum is lower in patients with metabolic syndrome such as diabetes, arteriosclerosis and other chronic diseases.

PRIOR ART DOCUMENTS

Patent Documents

[Patent Document 1] International Publication No. WO 2012/090625

Non-Patent Documents

[Non-Patent Document 1] Goodenowe, D. B. et al., J. Lipid Res., Vol. 48, 2007, pp. 2485-2498

BRIEF SUMMARY OF THE INVENTION

Problem to be Solved by the Invention

When calculating phospholipids in human serum or plasma by the amount of phosphorus, choline phospholipids are the majority amounting to about 68%, followed by about 20% of sphingomyelin, and about 8% of lyso-type choline phospholipids, while ethanolamine phospholipids amount to only about 2 to 3%. Further, since the serum and plasma are not a cell membrane, plasmalogens contained there are a quite few as compared to red blood cells and white blood cells. Accordingly, it was difficult to measure the amount of plasmalogens in serum or plasma.

Recently, a method combining high performance liquid chromatography (HPLC) with tandem mass spectrometry (LC/MS/MS) has been developed for measuring the amount of ether phospholipids in serum or plasma.

In addition, there has been a method, where radioactive iodine is reacted with vinyl ether bonds, then HPLC fractionates each ether phospholipid to measure the radioactivity by a gamma counter (γ-counter).

However, since LC/MS/MS and gamma counter are expensive, the measuring method of using either is not suitable for a general clinical testing.

Under these circumstances, the present inventors had studied extensively for the purpose of providing a method for measuring the amount of plasmalogens in samples, in particular serum or plasma, in an easy and inexpensive manner.

As a consequence, the present inventors found out that, by providing a specific processing with serum or plasma samples and by using HPLC with Evaporative Light Scattering Detector (ELSD) or Mass Spectrometer (MS), a fluorescence plate reader or a plate reader, it enables to measure the amount of plasmalogens in samples with high accuracy in an easy, convenient and inexpensive manner. The present invention was so completed.

Solution to the Problem

In one aspect, the present invention provides a method for quantifying plasmalogens contained in a sample comprising:

(A) a step of providing hydrolysis processing of a sample, after which lipid extraction is provided to obtain a lipid sample.

In one embodiment, the sample is serum or plasma.

In one embodiment, the plasmalogens are ethanolamine plasmalogens or choline plasmalogens.

In one embodiment, the hydrolysis processing is performed by phospholipase A1 (PLA1).

In one embodiment, the lipid extraction process is performed by a mixture of hexane and isopropanol (3:2, v/v), or chloroform and methanol (1:2, v/v).

In one aspect, the above-mentioned method for quantifying plasmalogens contained in a sample may further comprise:

(B) a step of subjecting the lipid sample obtained by the step (A) to a measurement.

In one embodiment, the measurement in the step (B) is performed by High Performance Liquid Chromatography (HPLC).

In one embodiment, the HPLC uses Evaporative Light Scattering Detector or Mass Spectrometer as a detector.

In one aspect, the above-mentioned method for quantifying plasmalogens contained in a sample may further comprise:

(B') a step of processing/reacting the lipid sample obtained by the step (A) with glycerophospholipid specific phospholipase D (GPL-PLD) to get an ethanolamine or a choline; and (C') a step of processing/reacting the ethanolamine or choline obtained by the step (B') with an amine oxidase or a choline oxidase to produce hydrogen peroxide ($H_2O_2$), respectively; and (D') a step of reacting the hydrogen peroxide ($H_2O_2$) produced by the step (C') with a fluorescent reagent in the presence of a peroxidase to produce a fluorescent compound to measure by a fluorescence plate reader; or (D") a step of reacting the hydrogen peroxide ($H_2O_2$) produced by the step (C') with coloring reagents in the presence of a peroxidase to produce a colored compound to measure by a plate reader.

The sequence of the addition of GPL-PLD, an amine oxidase or a choline oxidase, a fluorescent reagent or coloring reagents, and a peroxidase is not particularly limited. In one embodiment, the lipid sample obtained by the step (A) may be added with a combination of GPL-PLD and an amine oxidase (or a choline oxidase), and then added with a combination of a fluorescent reagent (or coloring reagents) and a peroxidase. In one embodiment, the lipid sample may be added with a combination of GPL-PLD, an amine oxidase (or a choline oxidase), a fluorescent reagent (or coloring reagents), and a peroxidase. In one embodiment, the lipid sample may be added with an amine oxidase (or a choline oxidase), and then added with GPL-PLD, and finally added with a combination of a fluorescent reagent (or coloring reagents) and a peroxidase. As depicted FIG. 5, the lipid sample obtained by the step (A), wherein a sample is hydrolyzed by PLA1, after which lipid extraction is provided, goes through reactions of steps (B'), (C') and (D' or D") sequentially to obtain a fluorescent compound or a colored compound for quantifying plasmalogens.

In one embodiment, the fluorescent reagent is Amplex Red and the fluorescent compound is resorufin. The coloring reagents are 4-aminoantipyrine and N-ethyl-N-(2-hydroxy-3-sulfopropyl)-toluidine (TOOS).

In one embodiment, after the step (A) and before the step (B or B'), unnecessary water-soluble substances are removed by using alcohol, sodium sulfate, water or any combination thereof.

In one aspect, the present invention provides a method for examining a subject to determine a risk of developing a disease that is closely associated with a change in the amount of plasmalogens comprising:

(1) a step of quantifying plasmalogens according to any one of the methods described above to quantify plasmalogens contained in a sample derived from a subject; and (2) a step of comparing the amount of plasmalogens in the sample measured at the step (1) with the amount of plasmalogens in a sample derived from a healthy subject.

In one embodiment, the subject is a human mammal. In another embodiment, the subject is a non-human mammal.

In one embodiment, the method further comprises:

(3) a step of determining that a risk of developing a disease is high as a consequence of the step (2), in the case where the amount of plasmalogens contained in a sample derived from the subject measured at the step (1) is either less or greater than that of plasmalogens contained in a sample derived from a healthy subject.

In one embodiment, the disease is dementia, depression, brain fatigue, insomnia, Parkinson's disease, metabolic syndrome, diabetes or arteriosclerosis.

In one aspect, the present invention provides a biomarker for detecting a disease that is closely associated with a change in the amount of plasmalogens, wherein the biomarker comprises plasmalogens contained in serum or plasma.

In one embodiment, the plasmalogens are ethanolamine plasmalogens or choline plasmalogens.

In one aspect, the present invention provides a method for using plasmalogens contained in serum or plasma, as a biomarker for detecting a disease that is closely associated with a change in the amount of plasmalogens.

In one embodiment, the plasmalogens are ethanolamine plasmalogens or choline plasmalogens.

In one aspect, the present invention also provides a test kit for examining a subject of a risk of developing diseases that are closely associated with a change in the amount of plasmalogens comprising:

a reagent used for hydrolysis processing of a sample; and organic solvents for lipid extraction.

In one embodiment, the test kit further comprises glycerophospholipid specific phospholipase D.

In one embodiment, the test kit further comprises an amine oxidase or a choline oxidase, a peroxidase, and a fluorescent reagent or coloring reagents.

Effect of the Invention

According to the present invention, it enables to measure the amount of plasmalogens, in particular ethanolamine plasmalogens or choline plasmalogens, contained only in a small quantity in samples especially serum or plasma samples, with high accuracy in an easy, convenient and inexpensive manner. The measurement is achieved by using High Performance Liquid Chromatography (HPLC) with Evaporative Light Scattering Detector (ELSD) or Mass Spectrometer (MS), a fluorescence plate reader or a plate reader.

Moreover, such quantification methods enables to provide a method for examining a subject to determine or predict a risk of developing disease that is closely associated with a change in the amount of plasmalogens (increase or decrease), such as dementia, depression, brain fatigue, insomnia, Parkinson's disease, metabolic syndrome, diabetes or arteriosclerosis, etc.

Furthermore, using a biomarker for detecting the diseases, it enables to examine to determine the risk in an easy and safe manner, further at low cost.

DESCRIPTION OF EMBODIMENTS

Figure 1:
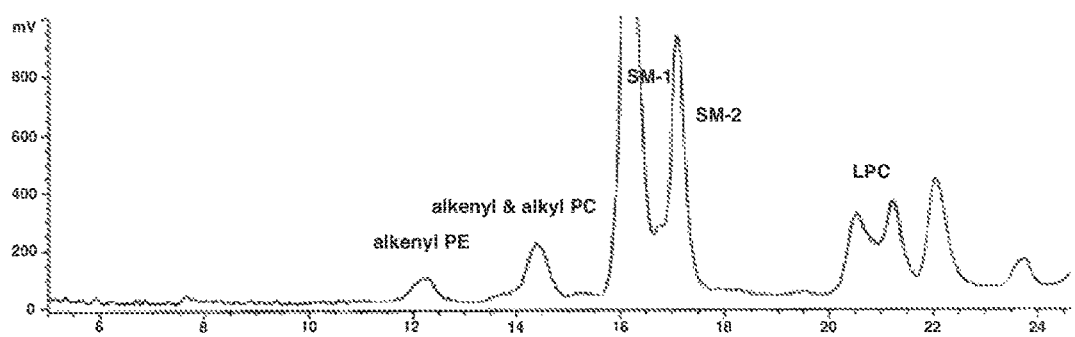
FIG. 1 is an HPLC chart depicting the total phospholipids after phospholipase A1 (PLA1) processing of plasma.

The followings describe embodiments of the present invention. Although the present invention is described mainly by preferred representative examples, the present invention is not limited to such examples.

According to one embodiment of the present invention, a method for quantifying plasmalogens contained in a sample comprises:

(A) a step of providing hydrolysis processing of a sample, after which lipid extraction processing is provided to obtain a lipid sample.

The sample may be any sample that contains or is expected to contain plasmalogens. The sample is preferably a biological sample derived from a subject. The subject may be mammals, i.e., humans and non-human mammals. The non-human mammals are, for example, pets, laboratory animals, livestock, and the like. Specifically, it may be dogs, cats, monkeys, cows, horses, sheep, goats, pigs, mice, rats, hamsters, rabbits, etc. The subject may also be a biological based material other than mammals that is expected to contain plasmalogens (e.g., shellfish etc.). Further, as long as it is expected to contain plasmalogens, the subject may be a plant tissue, seawater, natural water, fruit juice, beverage, waste liquid, etc.

The biological sample derived from a subject includes a subject-derived tissue, cell, body fluid (such as blood (whole blood, plasma, serum, blood cell, red blood cell membrane, etc.), cerebrospinal fluid, urine, lymph, saliva, sweat, etc.), extracts thereof and the like. The sample may be the one collected from a subject itself, or the one with which a certain processing is provided. According to the present invention, since it is possible to measure plasmalogens contained in samples even in a very small quantity, the sample may be preferably serum or plasma.

A publicly-known method may be used as a method for obtaining or preparing the sample. For example, in the case of collecting whole blood and serum or plasma, it is not particularly limited to either use or non-use of separating agent or anti-plasmin agent, etc.; nor is particularly limited to either use or non-use of EDTA, sodium fluoride, sodium citrate, heparin sodium, monoiodoacetic acid or other anticoagulant or glycolysis inhibitor. Specifically, serum or plasma may be obtained by using an ordinary, publicly known blood sampling method (such as syringe blood collection or vacuum blood collection) from a subject. For example, a blood sample may be obtained by being centrifuged (e.g., 1000*g, 5 minutes) to recover the supernatant.

The hydrolysis processing may be performed by specifically hydrolyzing an acyl bond at the sn-1 position, for example, a processing with phospholipase A1 (PLA1).

Said PLA1 hydrolyzes only an acyl bond, but does not act on ether bonds, at the sn-1 position in the sample. Therefore, the PLA1 processing hydrolyzes diacyl-type phospholipids, but not ether-type phospholipids.

The PLA1 is not particularly limited to its origin, as long as it can achieve the effect. The exemplary PLA1 may be the one derived from *Aspergillus orizae*. Such PLA1 may be purchased from, for example, Sigma-Aldrich Japan or Mitsubishi Kagaku Foods Corporation, etc. PLA1 manufactured by Sigma-Aldrich Japan is in liquid form, while those produced by Mitsubishi Kagaku Foods are in powder form containing 25% of PLA1.

The amount of the PLA1 may be selected as deemed fit, depending on the amount of sample. For example, in the case when processing serum or plasma using liquid PLA1 of Sigma-Aldrich Japan, the PLA1 is used preferably 0.01-0.50 µL, more preferably 0.04~0.20 µL, per the serum or plasma 10 µL.

Although the hydrolysis reaction by the PLA1 may be performed in suitable solvent, in particular buffer, such solvent may be selected as deemed fit, depending on PLA1 to be used. For example, it may be used 0.1M citrate buffer solution (pH 4.5). In that case, it may be performed by dissolving the PLA1 in the above buffer solution, preparing the PLA1 solution at a suitable concentration (e.g., 10-300 mg/µL in the case of using powder form of Mitsubishi Chemical Foods), thereby adding the PLA1 solution to 30~50 µL of serum or plasma.

The amount of the solvent may be any, as long as it may progress the hydrolysis reaction. Therefore, it is not particularly limited, but it is for example, preferably 1-200 µL, more preferably 5-200 µL, per 10 µL of serum or plasma.

The hydrolysis reaction conditions can be selected as deemed fit. For Example, the reaction may be performed at a temperature of preferably 30-70° C., more preferably 45-55° C., further preferably 50° C., to react for preferably 1-5 hr, more preferably 1-2 hr. In that case, pH is preferably pH3.5-5.5, more preferably pH4-5.

The hydrolysis reaction may be stopped by cooling.

Subsequent to the hydrolysis processing, the sample is subject to lipid extraction. This lipid extraction processing can remove free ethanolamine and choline in the sample. Therefore, it enables to quantify only ethanolamine plasmalogens and choline plasmalogens. It is difficult to quantify plasmalogens without the lipid extraction processing.

In terms of the lipid extraction, it is preferred to select a method capable of removing free ethanolamine and choline in the sample (e.g., a method using a chloroform-methanol mixed solvent or hexane/isopropanol mixed solvent). Meanwhile, it is ideal to remove in advance lysophospholipids having high water solubility, such as lyso-type ethanolamine phospholipids and lyso-type choline lipids generated by the hydrolysis processing. From this point of view, it is more preferred to select the method using hexane/isopropanol (3:2, v/v) mixed solvent (HIP method) than the Bligh & Dyer method using chloroform/methanol (1:2, v/v).

After the lipid extraction, a processing may be further provided to remove water-soluble substances such as metal (electrolyte), proteins, or sugars, which are present in lipid samples of the serum or plasma, by using alcohols, sodium sulfate, water or any combination thereof.

By hydrolysis processing with the samples (such as samples from a subject), preferably the one with PLA1, ether phospholipids (plasmalogens), lysophospholipids and sphingomyelin in the samples are intact, while phospholipids other than those are hydrolyzed.

In one embodiment, the above-mentioned method for quantifying plasmalogens contained in a sample may further comprise:

(B) a step of subjecting the lipid sample obtained by the step (A) to a measurement.

In one embodiment, the measurement in the step (B) is performed by High Performance Liquid Chromatography (HPLC). The HPLC measurement may be used with ELSD or LC/MS method with high accuracy in an easy, convenient and inexpensive manner.

As described above, the lipid samples of serum or plasma is obtained by extracting after PLA1 processing. By analyzing it with High Performance Liquid Chromatography (HPLC) equipped with a common detector, such as Evaporative Light Scattering Detector (ELSD) or Mass Spectrometer (MS), it enables to detect each plasmalogens present in serum or plasma as completely independent peaks from each other.

In that case, HPLC column includes, but is not limited to, a normal phase column, such as Lichrosphere 100 DIOL (250*3 mm, 5 μm). The eluting solution includes, but is not limited to:

Hexane/isopropanol/acetic acid (82:17:1, volume ratio)+ 0.08% triethylamine (mobile phase A) and Isopropanol/water/acetic acid (85:14:1, volume ratio)+ 0.08% triethylamine (mobile phase B), or Hexane/isopropanol/formic acid (82:17:1, volume ratio)+ 25% aqueous ammonia (mobile phase A) and Isopropanol/water/formic acid (85:14:1, volume ratio)+ 25% aqueous ammonia (mobile phase B), or Hexane/isopropanol/1M ammonium formate (82:17:1) (mobile phase A) and Isopropanol/water/1M ammonium formate (82:17:1) (mobile phase B), etc.

Figure 4:
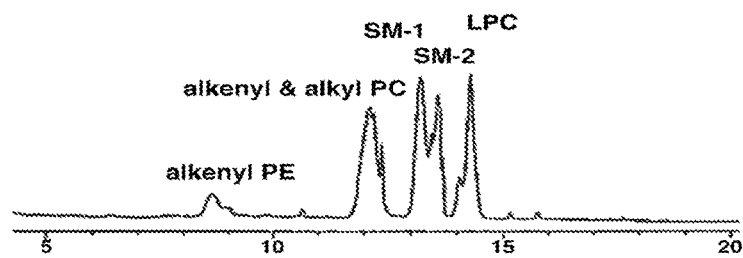
FIG. 4 is a mass spectrometry chart (total ion chromatogram (TIC)) depicting the total phospholipids in human plasma after phospholipase A1 processing.

It should be noted that, according to the present invention, the action of the PLA1 completely hydrolyzes diacyl-type phospholipids in serum or plasma. Thus, it may not be limited to the specific column or mobile phase, as long as the HPLC method is capable of complete separation of each phospholipid. FIG. 4 shows one of the examples. An area of each peak of the obtained chromatogram represents the content of each lipid component.

According to one embodiment of the present invention, the above-mentioned method for quantifying plasmalogens contained in a sample may further comprise:

(B') a step of processing/reacting the lipid sample obtained by the step (A) with glycerophospholipid specific phospholipase D (GPL-PLD) to get an ethanolamine or choline; and (C') a step of processing/reacting the ethanolamine or choline obtained by the step (B') with an amine oxidase or a choline oxidase to produce hydrogen peroxide ($H_2O_2$), respectively; and (D') a step of reacting the hydrogen peroxide ($H_2O_2$) produced by the step (C') with a fluorescent reagent in the presence of a peroxidase to produce a fluorescent compound to measure by a fluorescence plate reader; or (D") a step of reacting the hydrogen peroxide ($H_2O_2$) produced by the step (C') with coloring reagents in the presence of a peroxidase to produce a colored compound to measure by a plate reader.

Figure 5:
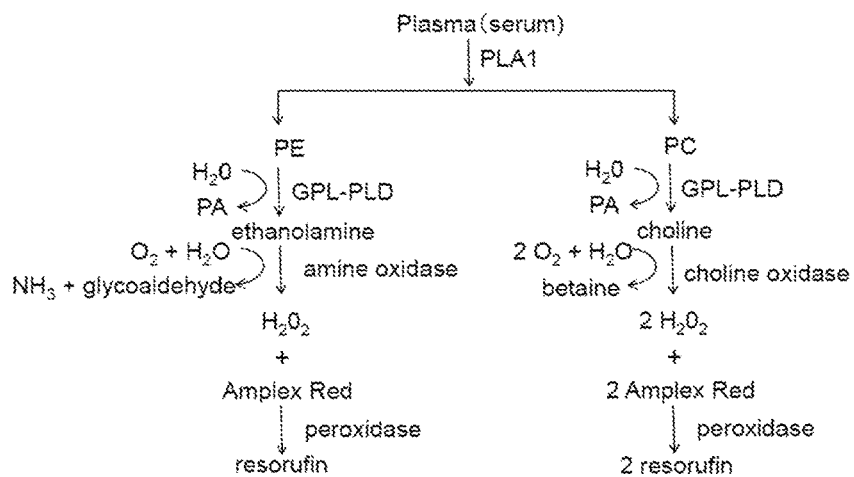
FIG. 5 is the strategy for enzymatic measurement of ethanolamine plasmalogenes (PE) or choline plasmalogenes (PC).

The sequence of the addition of GPL-PLD, an amine oxidase or a choline oxidase, a fluorescent reagent or coloring reagents, and a peroxidase is not particularly limited. In one embodiment, the lipid sample obtained by the step (A) may be added with a combination of GPL-PLD and an amine oxidase (or a choline oxidase), and then added with a combination of a fluorescent reagent (or coloring reagents) and a peroxidase. In one embodiment, the lipid sample may be added with a combination of GPL-PLD, an amine oxidase (or a choline oxidase), a fluorescent reagent (or coloring reagents), and a peroxidase. In one embodiment, the lipid sample may be added with an amine oxidase (or a choline oxidase), and then added with GPL-PLD, and finally added with a combination of a fluorescent reagent (or coloring reagents) and a peroxidase. As depicted FIG. 5, the lipid sample obtained by the step (A), wherein a sample is hydrolyzed by PLA1, after which lipid extraction is provided, goes through reactions of steps (B'), (C') and (D' or D") sequentially to obtain a fluorescent compound or a colored compound for quantifying plasmalogens.

The step (B') includes processing of the lipid sample obtained in the step (A) with glycerophospholipid specificity phospholipase D (GPL-PLD). The GPL-PLD hydrolyze a phosphate ester bond at the sn-3 position in the glycerol backborn. Therefore, ethanolamine and choline are generated.

By the process where ethanolamine and choline generated by the step (B') is subject to further processing with an amine oxidase to quantify ethanolamine plasmalogens or with a choline oxidase to quantify choline plasmalogens, hydrogen peroxide ($H_2O_2$) is generated.

In addition, in further process, to the solution containing the hydrogen peroxide is added a peroxidase and a fluorescent reagent to form the fluorescent compound (resorufin), which becomes possible to quantify plasmalogens (ethanol amine plasmalogens or choline plasmalogens) by a fluorescence plate reader. The above fluorescent reagent includes, but is not limited to, Amplex Red.

Further, a plate reader may be used instead of the fluorescence plate reader to quantify plasmalogens (ethanolamine plasmalogens or choline plasmalogens).

In that case, to the solution containing the hydrogen peroxide are added coloring reagents instead of the fluorescent reagent in the presence of a peroxidase, by which generate the coloring compound (violet-blue in the case when 4-aminoantipyrine and N-ethyl-N-(2-hydroxy-3-sulfopropyl)-toluidine (TOOS)) are used.

The coloring reagents can be selected from the publicly-known ones. The examples include phenol or its derivative, a combination of an aniline derivative and 4-aminoantipyrine, leuco dye, diphenylamine derivatives, triaryl imidazole derivatives, etc. Preferably, it is a combination of 4-aminoantipyrine and N-ethyl-N-(2-hydroxy-3-sulfopropyl)-toluidine (TOOS).

Measuring by a fluorescent plate reader or a plate reader enables to quantify even a very few amount of plasmalogens, in a relatively short time, simultaneously.

In measuring by the fluorescent plate reader or plate reader, it is selected a range of 450-600 nm. The degree of color development at a given wavelength thus represents the amount of lipid component. In the case of using a fluorescent plate reader, it is possible to quantify with stability and with higher sensitivity than a plate reader.

By using purified choline plasmalogens and ethanolamine phospholipids, it is possible to quantify their amounts by creating respective calibration curves.

It is possible to perform in the presence of a suitable surfactant for the processing with glycerophospholipid specific phospholipase D, the processing with an amine oxidase or a choline oxidase, the processing with a peroxidase and a fluorescent reagent, as well as the processing with a peroxidase and coloring reagents.

As the surfactant, it may be selected, preferably non-ionic surfactants, more preferably polyoxyethylene alkyl phenyl ether. The examples include Triton X-100.

The amount of the used surfactant, for example, is 0.01 to 10 mass %.

It may be performed by adjusting a buffer as deemed fit for the foregoing processing: one by the glycerophospholipid specific phospholipase D; and one by an amine oxidase or a choline oxidase, a peroxidase, and a fluorescence reagent or coloring reagents. The exemplary buffer includes Tris-HCl buffer, in particular 100 mM Tris-HCl buffer (pH 7.4) and the like.

Furthermore, the similar effect may be obtained by performing in a manner that the processing with glycerophospholipid specific phospholipase D, the processing with an amine oxidase or a choline oxidase, the processing with a peroxidase are carried out simultaneously instead of stepwise.

According to the present invention, by using the aforementioned method to quantify plasmalogens, it enables to compare the amount of plasmalogens in samples from a subject with that from a healthy subject to determine for the subject a risk of developing a disease that is closely associated with the change (increase or decrease) in the amount of plasmalogens.

According to the present invention, the examination method is the one for determining a risk of a subject developing a disease that is closely associated with a change in the amount of plasmalogens (increase or decrease) comprising:

(1) a step of quantifying plasmalogens according to any one of above methods, to quantify plasmalogens contained in a samples derived from a subject; and (2) a step of comparing the amount of plasmalogens in the sample measured at the step (1) with the amount of plasmalogens in a sample derived from a healthy subject.

The exemplary disease that is closely associated with the change in the amount of plasmalogens includes dementia, depression, brain fatigue, insomnia, Parkinson's disease, metabolic syndrome, diabetes, arteriosclerosis, and the like. Preferably, it is dementia, depression, brain fatigue, insomnia, Parkinson's disease, a metabolic syndrome, diabetes or arteriosclerosis. The exemplary dementia is degenerative dementia. Specifically, dementia associated with Parkinson's disease, frontotemporal dementia, Pick's disease, diffuse Lewy body disease, and Alzheimer's dementia can be exemplified.

The step (1) describes a step of quantifying plasmalogens contained in a sample derived from a subject according to the quantification method recited above, as the details are described above.

The step (2) is a step of comparing the amount of plasmalogens in the sample measured at the step (1) with the amount of plasmalogens in a sample derived from a healthy subject.

In other words, in this step, the followings are compared: (a) the amount of plasmalogens contained in a sample collected from a subject; and (b) the amount of plasmalogens contained in a sample collected from a healthy subject.

The term "the amount of plasmalogens contained in a sample collected from a healthy subject" means in general the amount of plasmalogens contained in a sample (e.g., blood plasma) that belongs to the identical species as the tested subject (e.g., mammals) and that does not suffer from the same disease at least or is preferably healthy.

According to the present invention, the examination method is provided as follows. By using a comparison result between (a) the amount of plasmalogens contained in a sample collected from a subject; and (b) the amount of plasmalogens contained in a sample collected from a healthy subject, it can determine if a risk is high or low of developing a disease that is closely associated with a change in the amount of plasmalogens (increase or decrease) for the subject.

When (a) is less or greater than (b), it is determined that the subject bears a high risk of developing a disease. In other words, the examination method may include further a following step: (3) a step of determining a risk of developing a disease is high as a consequence of the step (2), in the case where the amount of plasmalogens contained in samples derived from a subject measured at the step (2) is either less or greater than that of plasmalogens contained in a sample derived from a healthy subject.

The present invention encompasses a biomarker for detecting a disease that is closely associated with a change in the amount of plasmalogens contained in serum or plasma. It should be noted that, instead of plasminogen present in a living body, plasmalogens contained in the serum or plasma isolated from a living body is used as the biomarker for disease detection. Thus, the biomarker according to the present invention is the one for disease detection comprising plasmalogens extracted from serum or plasma. The biomarker according to the present invention has a feature that the amount of plasmalogens derived from a subject who develops the disease changes (decreases or increases) as compared to that from a healthy subject.

Therefore, by isolating the biomarker from the subject and the healthy subject respectively to measure the amount for comparison, it is possible to diagnose that the subject develops the said disease when the amount of plasmalogens derived from the subject is less or greater than that derived from the healthy subject.

It is preferred that the biomarker for disease detection comprises, among plasmalogens, ethanolamine plasmalogens or choline plasmalogens. Therefore, the present invention preferably includes the biomarker for disease detection comprising ethanolamine plasmalogens or choline plasmalogens contained in serum or plasma. According to the present invention, the biomarker can be easily exercised based on the above description.

The present invention also encompasses a test kit for examining a subject of a risk of developing a disease that is closely associated with a change in the amount of plasmalogens. According to the present invention, the test kit is provided with a reagent useful for quantifying plasmalogens contained in a sample, and an organic solvent for lipid extraction.

The exemplary reagent includes a reagent used for hydrolysis processing of samples, specifically, a reagent for hydrolyzing lipids contained in samples, and a reagent useful for producing ethanolamine or choline after the hydrolysis processing. More specifically, it may be phospholipase A1 (PLA1), its solvent (e.g. 0.1M citrate buffer solution), or glycerophospholipids specificity phospholipase D, and the like.

The exemplary organic solvent for lipid extraction includes chloroform, chloroform/methanol (preferably 1:2) mixture, hexane, hexane/isopropanol (preferably 3:2) mixture, and the like.

The kit may be provided with: a blood collection device, such as a blood collection syringe and blood collection tube; further, a reagent for the analysis by the fluorescent plate reader or plate reader, such as GPL-PLD, an amine oxidase, a choline oxidase, a peroxidase, a fluorescent reagent and coloring reagents. According to the present invention, the kit can be easily exercised based on the above description.

EXAMPLES

The followings describe the present invention with reference to examples. However, the present invention is not limited to these examples.

Example 1: Quantification of Plasmalogens in Plasma by HPLC-ELSD (1) Blood Collection
Venous blood was collected using a syringe.
To the blood so collected was added EDTA-Na as anticoagulant. This was used as human blood sample.
(2) Preparation of Plasma
The blood sample so obtained was centrifuged at 1000*g for 5 min, and supernatant (i.e. plasma) was recovered.
(3) Preparation of plasma sample
a. 50 μL of plasma was placed in an EPPENDORF TUBE®.
b. Phospholipase A1 (PLA1) solution was prepared by dissolving 25% of PLA1 powder (derived from *Aspergillus orizae*, manufactured by Mitsubishi Kagaku Foods) with 0.1M citric acid (pH4.5) at a concentration of 200 mg/mL.
c. 150 μL of the phospholipase A1 (PLA1) solution so obtained was added to plasma and well mixed, subject to reaction at a temperature of 50° C. for 1 hour.
d. To the reaction mixture was added 0.5 mL of chloroform/methanol (1:2), subject to vigorous mixing for 1 min, after which it was placed at a room temperature for 10 min.
e. The resulting mixture was centrifuged at 13,000 rpm for 10 minutes.
f. The chloroform layer was recovered and placed onto a separate conical glass tube.
g. The recovered chloroform layer was dried by a nitrogen gas to make it as a plasma sample, which was stored at a temperature of −30° C.
(4) HPLC Analysis of the Plasma Sample
The obtained plasma sample was again dissolved in 200 μL of hexane/isopropanol (3:2).
Then obtained plasma sample was injected into HPLC to analyze on the conditions below.
The result is shown in FIG. 1.
Conditions for HPLC
Device used: HPLC Agilent 1260 System (Agilent Technologies, Tokyo)
Column: Lichrosphere 100 DIOL (250*3 mm, 5 μm) (Merck, Tokyo)
Flow rate: 0.4 ml/min
Column temperature: 50° C.
Detection: ELSD (1290 Infinity ELSD, Agilent Technologies) Gain 5, N2 gas flow rate 0.99 LSM, evaporator temperature 60° C.
Mobile Phase:
(A) hexane/isopropanol/acetic acid (82:17:1, v/v, +0.08% triethylamine)
(B) isopropanol/water/acetic acid (85:14:1, v/v, +0.08% triethylamine) TABLE 1 shows a gradient of mobile phases (A) and (B).

TABLE 1

| Time (min) | Mobile phase (A) (%) | Mobile phase (B) (%) |
|---|---|---|
| 0 | 96 | 4 |
| 21 | 63 | 37 |
| 25 | 15 | 85 |
| 26 | 15 | 85 |
| 29 | 96 | 4 |
| 36 | 96 | 4 |

According to FIG. 1, it was found that by directly processing human plasma with PLA1, diacyl phospholipids (acyl PE, acyl PC, acyl PI) were completely decomposed. Thus, after the PLA1 processing, the quantification becomes clear, as each plasmalogens can be detected by independent peaks respectively.

Figure 2:
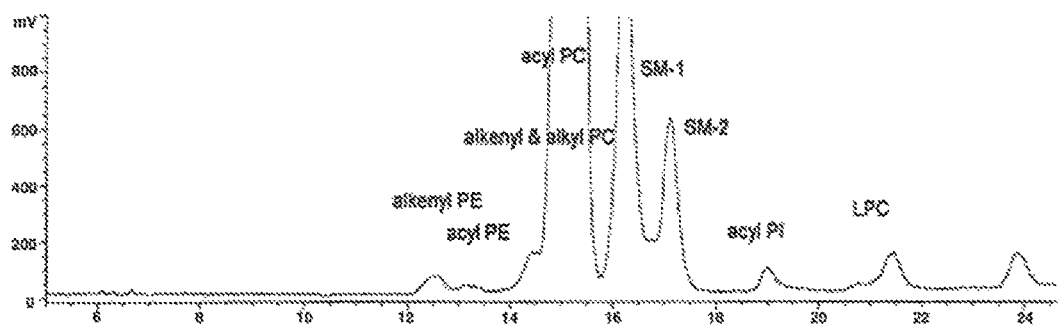
FIG. 2 is an HPLC chart depicting the total phospholipids in plasma.

On the other hand, FIG. 2 depicts HPLC chart representing the total phospholipids in plasma without the PLA1 processing. There is an extremely small amount of ethanolamine plasmalogens and choline plasmalogens contained in human plasma. According to FIG. 2, it was found that if the total lipids (without processing) were analyzed by the above HPLC method, the separation between diacyl-type phospholipids and ether-type phospholipids resulted in incomplete.

Therefore, according to the present invention, it is evident that it enables to quantify the amount of plasmalogens contained even in a small quantity in serum or plasma, with high accuracy in an easy and convenient manner, further inexpensively.

Figure 3:
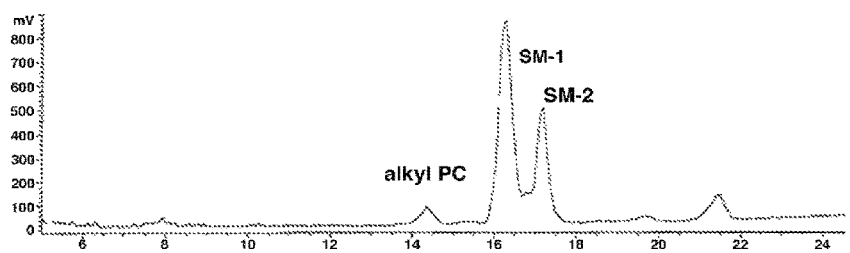
FIG. 3 is an HPLC chart depicting the total phospholipids after phospholipase A1 processing and hydrochloric acid hydrolysis.

FIG. 3 depicts the total phospholipids in plasma that was provided phospholipase A1 processing and hydrochloric acid treatment. When phospholipids are provided hydrochloric acid hydrolysis, alkenyl phospholipids (plasmalogens) are decomposed, while acyl phospholipids and alkyl phospholipids are not decomposed. According to FIG. 3, it is indicated that ether phospholipids having choline residue in human plasma contain about 50% of alkyl phospholipids (alkyl PC).

Further, taking into consideration the results shown in FIG. 1 and FIG. 3, it was found that phospholipids in human serum or plasma are constituted by diacyl choline phospholipids (acyl PC), sphingomyelin (SM-1, SM-2), lyso choline phospholipids (LPC), diacyl ethanolamine phospholipids (acyl PE), diacyl inositol phospholipids (acyl PI), and ether phospholipids, such as alkenyl ethanolamine phospholipids (alkenyl PE), alkenyl, and alkyl choline phospholipids (alkenyl PC, alkyl PC) (See FIG. 2).

Example 2: HPLC-MS Analysis of Human Plasma

After the PLA1 processing was provided to human plasma then subjected to the lipid extraction processing as [00125], it was injected to HPLC for the measurement of plasmalogens by linking to a mass spectrometer (MS).

In this example, like above, HPLC Agilent 1260 System (Agilent Technologies, Tokyo) was used as HPLC.

In terms of the conditions, the similar ones were used except that Ascentis Express HILLIC 150*2.1 mm (2.7 μm) (Sigma, Tokyo) was used as a column, that mobile phases were (A) acetonitrile and (B) 1.0 mM of ammonium formate (pH3 adjusted by formic acid), and that a flow rate was set by 0.2 mL/min.

As MS, Agilent 6130 (Agilent Technologies, Tokyo) was used.

The result is shown in FIG. 4.

According to FIG. 4, it is found that diacyl-type phospholipids are completely decomposed by the acting of PLA1. Therefore, it is evident that no limit is necessary to a specific column or mobile phase, as long as HPLC is capable of mutual separation of each phospholipid. Furthermore, it is evident that it enables to analyze plasmalogens in serum or plasma by mass spectrometry that is directly linked to HPLC.

Example 3: Quantifying Ethanolamine Plasmalogens in Plasma with a Fluorecent Reagent (1) Blood Collection Venous blood was collected using a heparin-contained blood collection tube (manufactured by Terumo Corporation). The venous blood was used as a human blood sample.

(2) Preparation of Plasma

The blood sample so obtained was centrifuged at 1000*g for 5 min, and supernatant (i.e. plasma) was recovered.

(3) Preparation of plasma samples a. 20-50 μL of plasma was placed in an EPPENDORF TUBE®.

b. Phospholipase A1 (PLA1) (derived from *Aspergillus orizae*, manufactured by Sigma-Aldrich Japan) had been 2-fold diluted by 0.1M citric acid buffer solution (pH4.5). To the plasma was added 10 μL of the diluted PLA1, and the mixture was well mixed at a temperature of 45° C. for 60 min.

c. Further, 800 μL of hexane/isopropanol (3:2) was added and then placed in an ultrasonic bath for 5 min.

d. To the resulting mixture, 400 μL of aqueous solution of sodium sulfate (1 g of $Na_2SO_4$ was dissolved in 15 mL of water) was added and mixed for 30 sec.

e. The resulting mixture was centrifuged at 1000*g for 5 min.

f. 400 μL of the upper layer (hexane layer) was recovered.

g. To the remaining lower layer (aqueous layer), 400 μL of hexane/isopropanol (7:2) was added and mixed for 10-20 sec.

h. Those obtained were centrifuged at 1000*g for 5 minutes, and 300 μL of the hexane layer was recovered.

i. The combined upper layer (hexane layer) was dried with nitrogen gas to make it as plasma samples, and stored at a temperature of −30° C.

(4) Preparation of Various Reagent Solutions (4-1) Preparation of Reagent Solution 1

Reagent Solution 1 was obtained by mixing substances shown in TABLE 2, then prepared with 100 mM tris-hydrochloric acid buffer solution (pH 7.4).

TABLE 2

| Prescription for Reagent Solution 1 | |
|---|---|
| Glycerophospholipid specific phospholipase D*[1] | 50 U/mL (2 μL/mL) |
| Amine oxidase*[2] | 2 U/mL |
| Triton X-100 | 0.2% |

*[1]manufactured by Sigma-Aldrich Japan.
*[2]manufactured by Asahi Kasei Pharma Corporation (4-2) Preparation of Reagent Solution 2

Reagent Solution 2 was obtained by mixing substances show in TABLE 3, then prepared with 100 mM tris-hydrochloric acid buffer solution (pH 7.4).

TABLE 3

| Prescription for Reagent Solution 2 | |
|---|---|
| Peroxidase | 5 U/mL |
| Amplex-Red*[3] | 100 μL |
| Calcium chloride | 1.5 mM |

*[3]manufactured by Molecular Probes.

(5) Analysis of Plasma Samples by Fluorescence Plate Reader a. The stored plasma samples (lipid samples) and standard phospholipids (phosphatidyl ethanolamine) were added to 20 μL of 1% Triton X-100, subject to dissolution.

b. 10, 20, 30, 40 and 50 μL of the plasma samples were dispensed to wells of a microplate reader.

c. 50 μL of Reagent Solution 1 was added and mixed, placed at a temperature of 37° C. for 30 min.

d. Further, 50 μL of Reagent Solution 2 was added, and placed at a temperature of 37° C. for 30 min.

e. The measurement of the resulting solution was performed at wavelength Ex 540 nm, wavelength Em 590 nm.

(6) Calculation of the amount of ethanolamine plasmalogens in the plasma samples A calibration curve was created from the measured value of the phosphatidyl ethanolamine (PE).

Using the above calibration curve, the amount of ethanolamine plasmalogens in the plasma samples was calculated from the measured value of the plasma samples.

Figure 8:
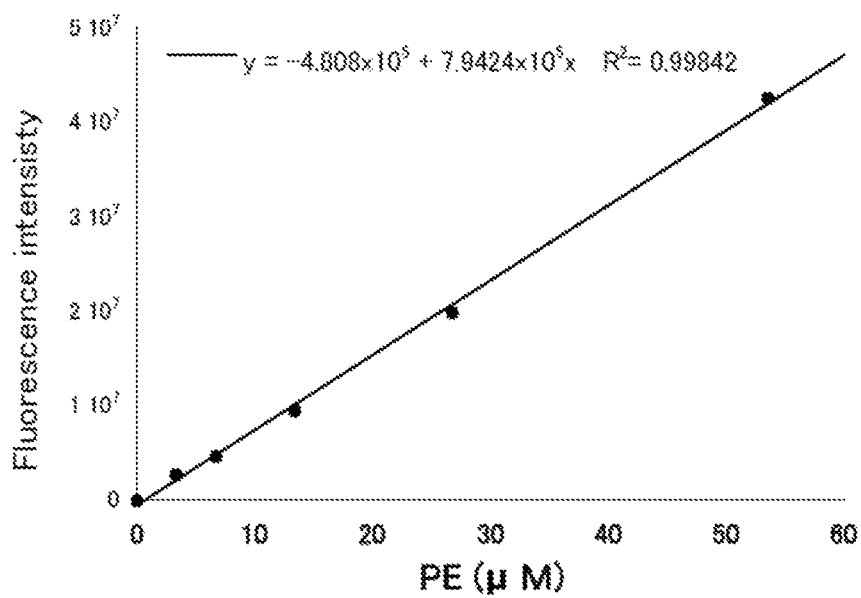
FIG. 8 is a standard curve for (a) ethanolamine plasmalogens and (b) choline plasmalogens (pl-PC).
Figure 8:
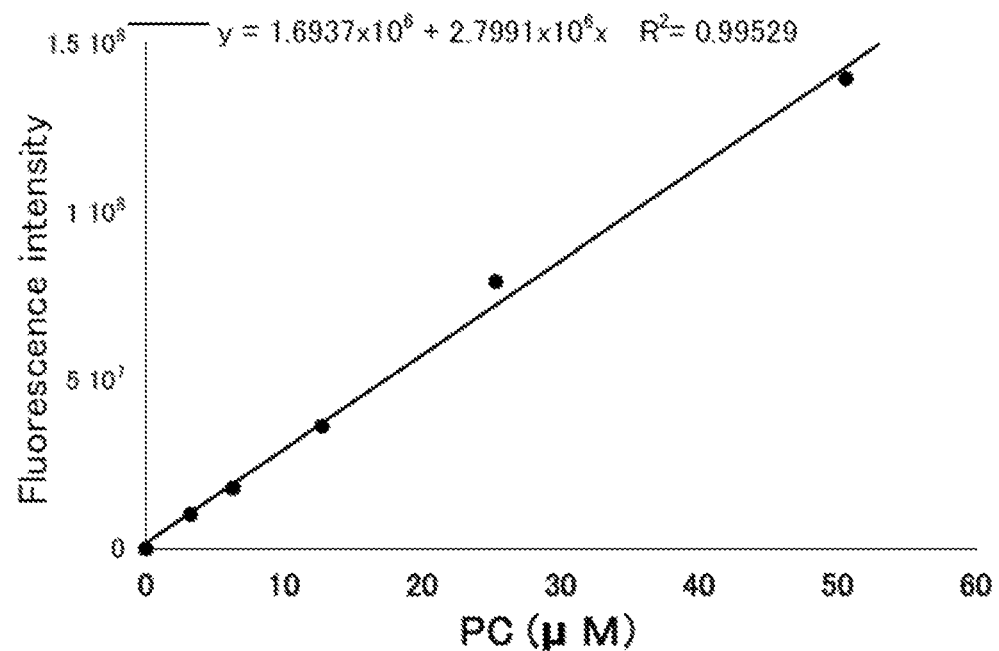

The result is shown in FIG. 8 (*a*).

Figure 6:
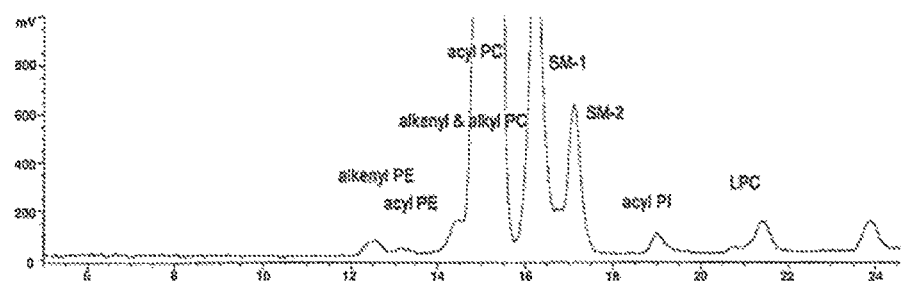
FIG. 6 is HPLC chart, where (a) represents the total phospholipids in human plasma, and (b) represents those after the phospholipase A1 processing.
Figure 6:
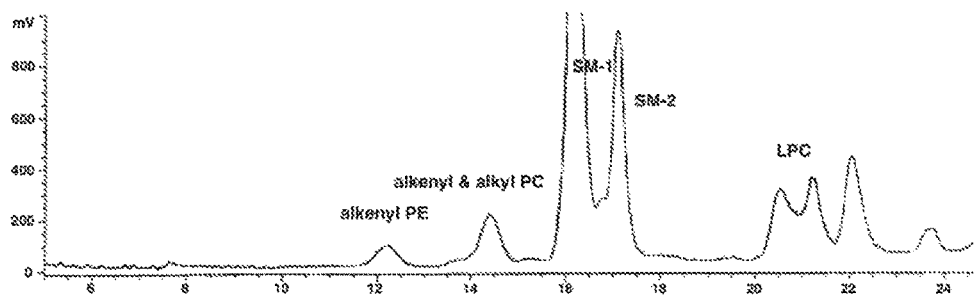

From FIG. 6, it is found that diacyl type ethanolamine phospholipids are completely decomposed by directly processing the human plasma with phospholipase A1.

Figure 7:
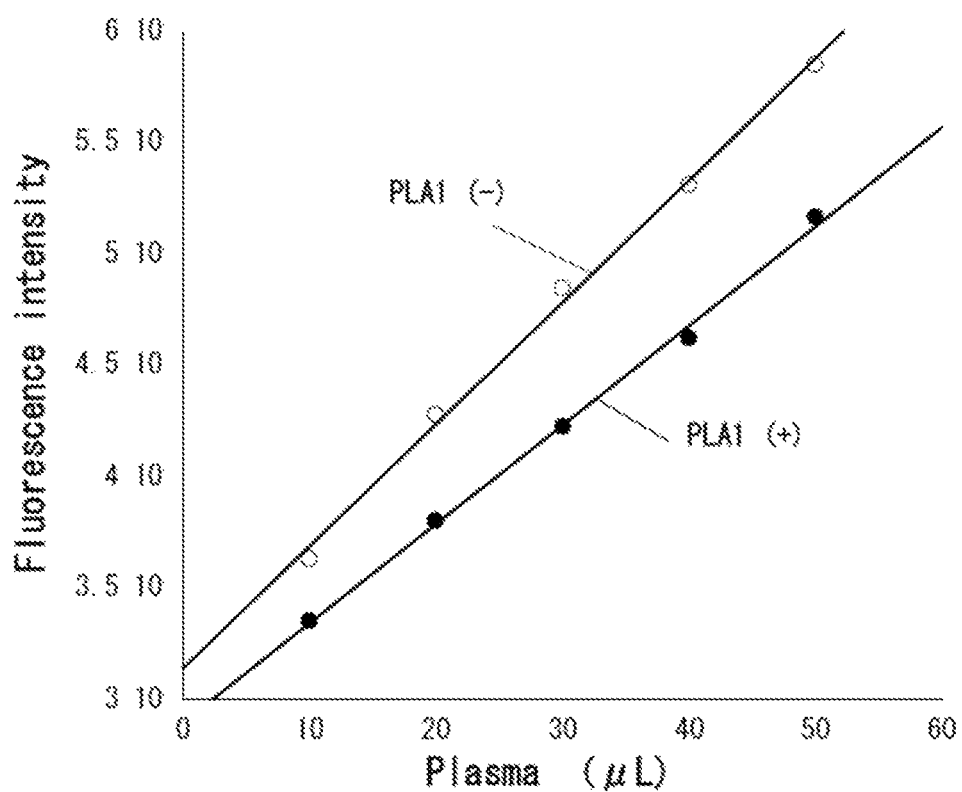
FIG. 7 is a measurement result of ethanolamine plasmalogens (pl-PE) in human plasma using a fluorescence plate reader with or without phospholipase A1 processing.

Accordingly, as shown in FIG. 7, only ethanolamine plasmalogens are measured by processing with phospholipase A1 to the human plasma, thereafter providing lipid extraction and a certain enzymatic processing, subject to fluorophotometric analysis. Therefore, according to the present invention, it enables to quantify ethanolamine plasmalogens even in a very few amount contained in serum or plasma, with high accuracy and in an easy and convenient manner, simultaneously and on a massive scale.

In the case where the processing with phospholipase A1 is not provided, both ethanolamine plasmalogens and diacyl type ethanolamine phospholipids are measured.

Example 4: Quantifying Choline Plasmalogens in Plasma with a Fluorescent Reagent Quantifying choline plasmalogens in plasma was performed by the similar method to EXAMPLE 3, except using Reagent Solution 3 instead of Reagent Solution 1. Reagent Solution 3 was obtained by mixing substances shown in TABLE 4, then prepared with 100 mM tris-hydrochloric acid buffer solution (pH 7.4).

Using the calibration curve (FIG. 8 (b)) created from the measured value of phosphatidyl choline (PC), the amount of choline plasmalogens in the plasma samples are calculated based on the measured value of the plasma samples.

Figure 9:
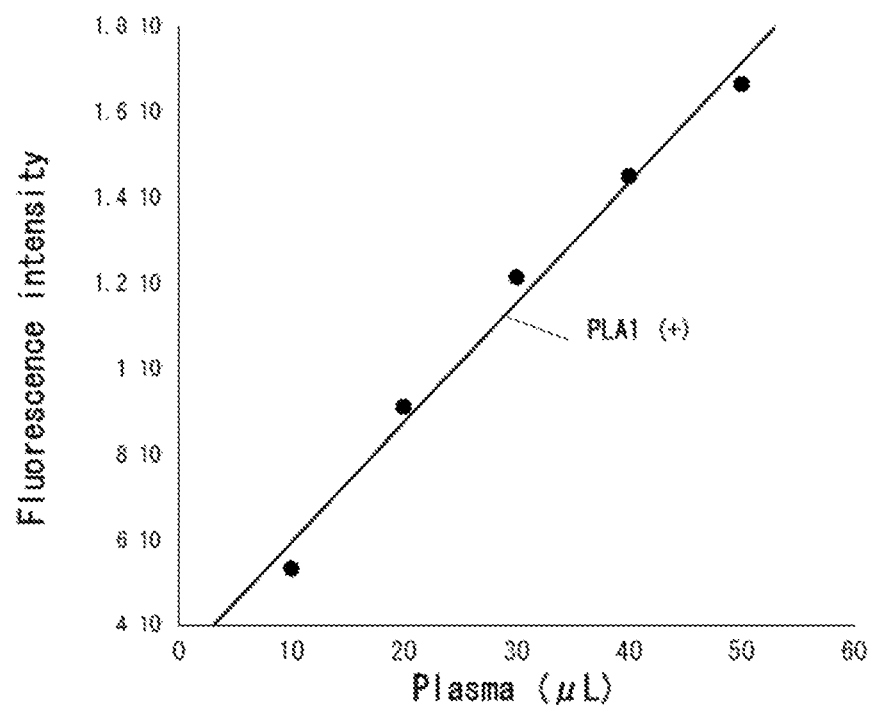
FIG. 9 is a measurement result of choline plasmalogens (pl-PC) in human plasma using a fluorescence plate reader.

The results are shown in FIG. 9.

TABLE 4

| Prescription for Reagent Solution 3 | |
|---|---|
| Glycerophospholipid specific phospholipase D*[4] | 50 U/mL (2 μL/mL) |
| Choline oxidase*[4] | 2 U/mL |
| Triton X-100 | 0.2% |

*[4]manufactured by Sigma-Aldrich Japan.

By reference to FIG. 6, it is found that human plasma contains by far diacyl type choline phosopholipids (PC) than choline plasmalogens. Therefore, without the present invention, it is not possible to quantify choline plasmalogens contained in a very few amount in serum or plasma.

Example 5: Quantifying Ethanolamine Plasmalogens in Plasma with Coloring Reagents Quantifying ethanolamine plasmalogens in plasma is performed by the similar method to EXAMPLE 3, except using Reagent Solution 4 instead of Reagent Solution 2 and a plate reader to measure at wavelength 595 nm instead of a fluorescence plate reader. Reagent Solution 4 was obtained by mixing substances shown in TABLE 5, then prepared with 100 mM tris-hydrochloric acid buffer solution (pH 7.4).

Figure 10:
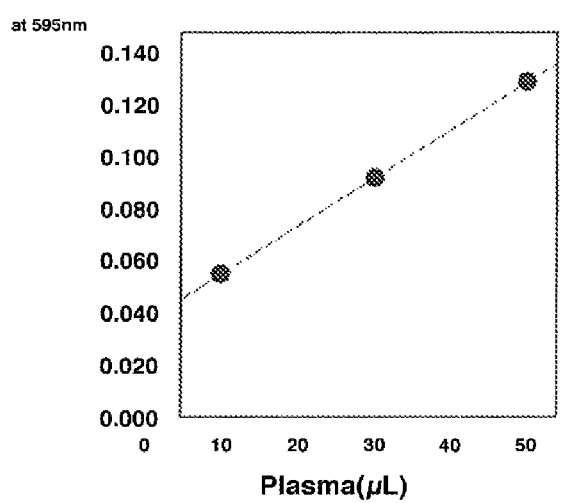
FIG. 10 is a measurement result of ethanolamine plasmalogens (pl-PE) in human plasma using a plate reader.

The results are shown in FIG. 10.

TABLE 5

| Prescription for Reagent Solution 4 | |
|---|---|
| Peroxidase | 5 U/mL |
| N-ethyl-N-(2-hydroxy-3-sulfopropyl)-toluidine (TOOS) | 2 mM |
| 4-aminoantipyrine | 1 mM |
| Calcium chloride | 1.5 mM |
| Triton X-100 | 0.1% |

As shown in FIG. 10, it is evident that the present invention enables to quantify ethanolamine plasmalogens contained even in a very few amount in serum or plasma simultaneously and in a large scale by using a plate reader.

Example 6: Quantifying Choline Plasmalogens in Plasma with Coloring Reagents Quantifying choline plasmalogens in plasma was performed by the similar method to EXAMPLE 5, except using Reagent Solution 3 instead of Reaction Solution 1.

Figure 11:
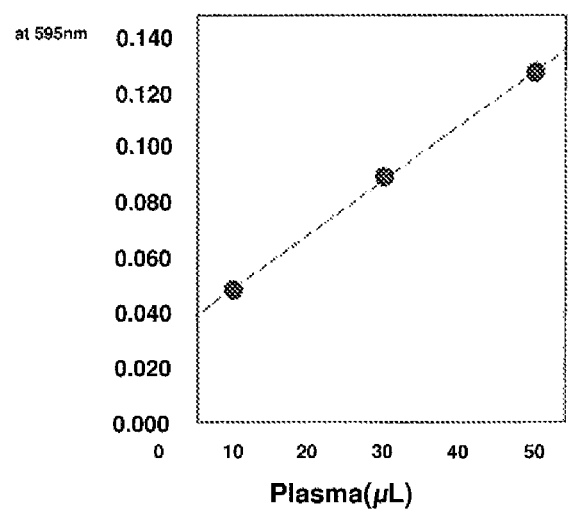
FIG. 11 is a measurement result of choline plasmalogens (pl-PC) in human plasma using a plate reader.

The results are shown in FIG. 11.

Example 7: Quantifying Ethanolamine Plasmalogens in Human Red Blood Cell Membrane with a Fluorescent Reagent (1) Preparation of Human Red Blood Cell Membrane
a. Washed red blood cell was prepared from a human blood.
b. 1 mL of the obtained washed red blood cell was hemolyzed and washed using tris-HCl buffer solution to prepare the red blood cell membrane.

(2) Preparation of Lipid Sample in Human Red Blood Cell Membrane
a. From the 100 μL of the red blood cell membrane, the total lipids were extracted by using chloroform-methanol (1:2, 3000 μL) and dried.
b. The the total lipid obtained was added by 10 μL of 2-fold diluted solution of phospholipase A1 (PLA1) (manufactured by Sigma-Aldrich Japan), subject to well mixing for reaction at a temperature of 45° C. for 1 hour.
c. To the resulting mixture, 800 μL of hexane/isopropanol (3:2) was added and mixed to extract lipids, which were dried with nitrogen gas to obtain a lipid sample.

(3) Analysis of Red Blood Cell Membrane Sample by Fluorescence Plate Reader

Quantifying ethanolamine plasmalogens were performed by a method similar to EXAMPLE 3 for the lipid sample obtained.

Figure 13:
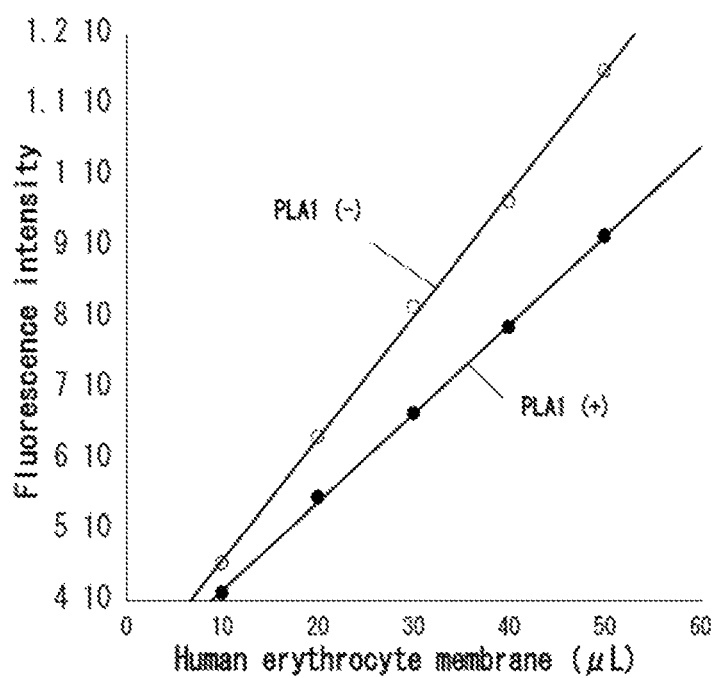
FIG. 13 is a measurement result of ethanolamine plasmalogens (pl-PE) of human erythrocyte membrane using a fluorescence plate reader with and without the phospholipase A1 processing.

The results are shown in FIG. 13.

Figure 12:
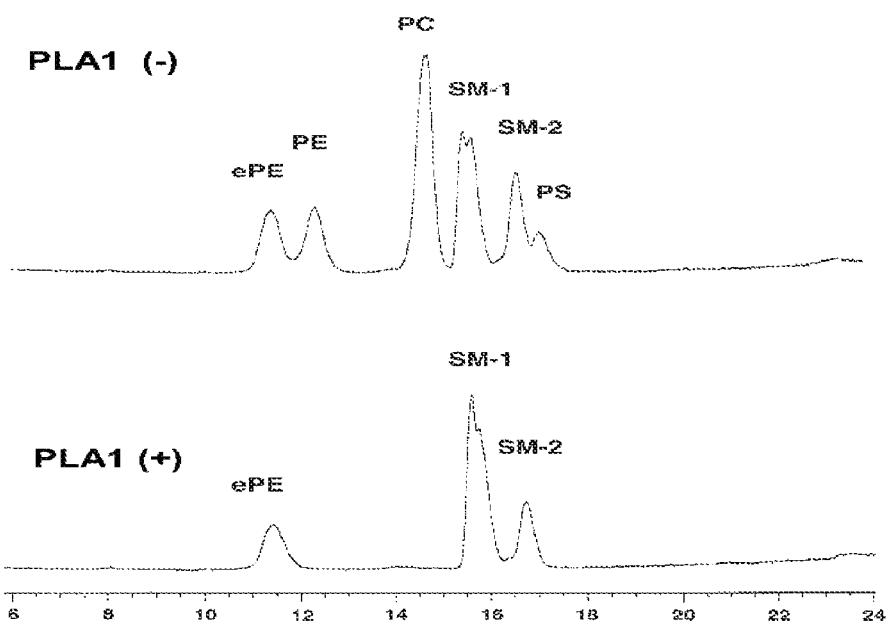
FIG. 12 is HPLC chart represents the total phospholipids in human erythrocyte membrane with (lower) and without (upper) the phospholipase A1 processing.

It is found from FIG. 12 that diacyl type ethanolamine phospholipids (PE) are completely decomposed by directly processing extraction liquid from the human red blood cell membrane with phospholipase A1.

Accordingly, as shown in FIG. 13, only ethanolamine plasmalogens (pl-PE) can be measured by processing the lipid extract from a human red blood cell membrane with phospholipase A1, after which are provided processing of lipid extraction and processing by certain enzyme to measure by fluorophotometric analysis.

It is found from FIG. 12 that without processing with phospholipase A1, it is measured ethanolamine plasmalogens and diacyl type ethanolamine phospholipids altogether.

Example 9: Quantifying Choline Plasmalogens in Chicken Breast (1) Preparation of Lipid Sample
a. The total lipids were extracted from 1 g of chicken breast meat, using 3000 μL of chloroform-methanol (1:2), subject to dryness with nitrogen gas.
b. To the total lipids obtained, 10 μL of 2-fold diluted phospholipase A1 (PLA1) (manufactured by Sigma-Aldrich Japan) was added, well mixed at a temperature of 45° C. for 1 hour.
c. To the resulting mixture, 800 μL of hexane/isopropanol (3:2) was added, mixed to extract lipids, and dried with nitrogen gas to obtain a lipid sample.

(2) Analysis of Chicken Breast Meat Sample by Fluorescent Plate Reader

The lipid samples obtained was quantified for plasmalogens according to the similar methods to EXAMPLE 4.

Figure 15:
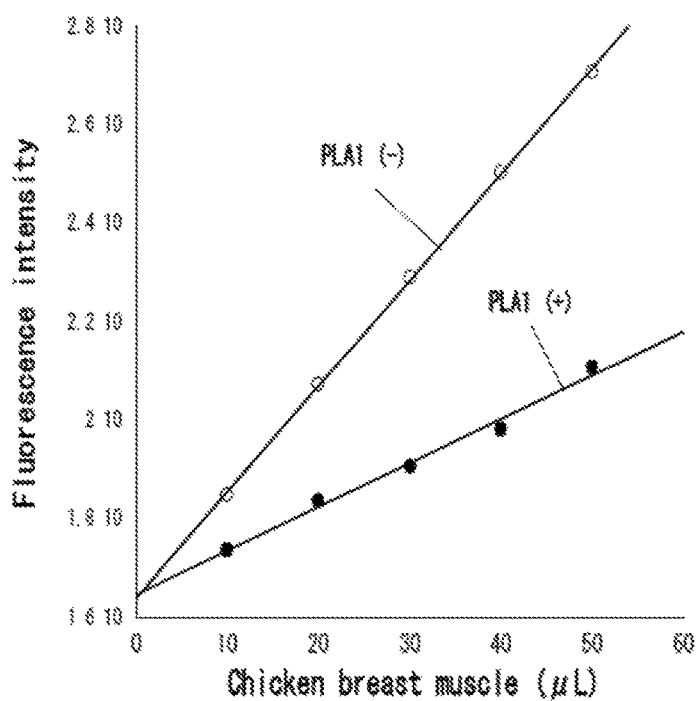
FIG. 15 is a measurement result of choline plasmalogens (pl-PC) of chicken breast muscle using a fluorescence plate reader.

The results are shown in FIG. 15.

As shown in FIG. 15, only choline plasmalogens can be measured by processing the lipid extract from a chicken breast meat with phospholipase A1, after which are provided processing of lipid extraction and processing by certain enzyme to measure by fluorophotometric analysis. Therefore, it is evident that the present invention enables to quantify choline plasmalogens contained in tissues of chicken breast meat, with high accuracy and in an easy and convenient manner, simultaneously and on a massive scale.

Figure 14:
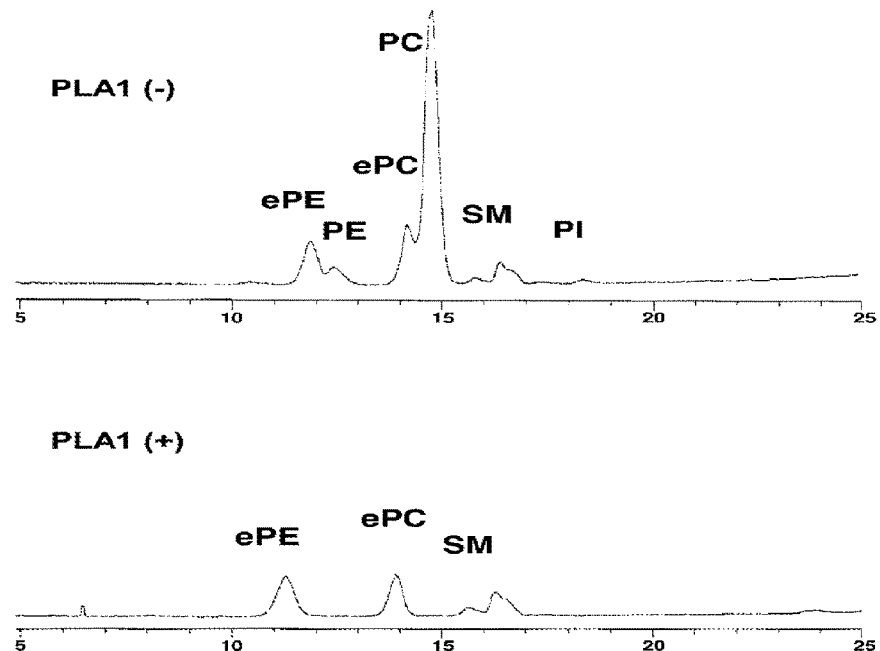
FIG. 14 is HPLC chart, where represents the total phospholipid of chicken breast muscle (upper), and represents those after the phospholipase A1 processing (lower).

It is found from FIG. 15 that without processing with phospholipase A1, it is measured choline plasmalogens (ePC) and diacyl choline phospholipids (PC) altogether. In addition, it is found from FIG. 14 that a chicken breast meat contains diacyl type choline phospholipids (PC) by far more amount as compared to choline plasmalogens.

INDUSTRIAL APPLICABILITY

According to the present invention, it enables to quantify plasmalogens contained in samples even in a very few amount, with high accuracy in an easy, convenient and inexpensive manner.

Further, by using such a quantifying method, it enables to determine or predict a risk of a subject developing a disease that is closely associated with a change in the amount of plasmalogens, such as dementia, depression, brain fatigue, insomnia, Parkinson's disease, metabolic syndrome, arterial sclerosis, etc. Therefore, it is expected to be widely utilized in the field of medicine.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for quantifying plasmalogens contained in a sample comprising:
   (A) a step of providing hydrolysis processing of a sample, after which lipid extraction is performed to obtain a lipid sample;
   (B') a step of reacting the lipid sample obtained by the step (A) with glycerophospholipid specific phospholipase D to get an ethanolamine or a choline; and
   (C') a step of reacting the ethanolamine or choline obtained by the step (B') with an amine oxidase or a choline oxidase to produce hydrogen peroxide ($H_2O_2$) respectively; and
   (D') a step of reacting the hydrogen peroxide ($H_2O_2$) produced by the step (C') with a fluorescent reagent in the presence of a peroxidase to produce a fluorescent compound, and measuring the fluorescent compound by a fluorescence plate reader; or
   (D") a step of reacting the hydrogen peroxide ($H_2O_2$) produced by the step (C') with coloring reagents in the presence of a peroxidase to produce a colored compound, and measuring the colored compound by a plate reader.

2. The method for quantifying plasmalogens according to claim 1, wherein the sample is serum or plasma.

3. The method for quantifying plasmalogens according to claim 1, wherein the plasmalogens are ethanolamine plasmalogens or choline plasmalogens.

4. The method for quantifying plasmalogens according to claim 1, wherein the hydrolysis processing is performed by phospholipase A1 (PLA1).

5. The method of quantifying plasmalogens according to claim 1, wherein the lipid extraction process is performed by a mixture of hexane/isopropanol in a volume ratio of 3:2 or chloroform-methanol in a volume ratio of 1:2.

6. The method for quantifying plasmalogens according to claim 1, wherein the fluorescent reagent is 10-acetyl-3,7-dihydropenoxazine.

7. The method for quantifying plasmalogens according to claim 1, wherein the coloring reagents are 4-aminoantipyrine and N-ethyl-N-(2-hydroxy-3-sulfopropyl)-toluidine (TOOS).

8. The method of quantifying plasmalogens according to claim 1, wherein after the step (A) and before the step (B'), water-soluble substances are removed by using alcohol, sodium sulfate, water or any combination thereof.

* * * * *